(12) United States Patent
Rahn (10) Patent No.: US 10,332,257 B2
(45) Date of Patent: Jun. 25, 2019

(54) VISUALIZATION OF AT LEAST ONE CHARACTERISTIC VARIABLE

(71) Applicant: Siemens Healthcare GmbH, Erlangen (DE)

(72) Inventor: Norbert Rahn, Forchheim (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 0 days.

(21) Appl. No.: 16/018,187

(22) Filed: Jun. 26, 2018

(65) Prior Publication Data

US 2019/0005643 A1 Jan. 3, 2019

(30) Foreign Application Priority Data

Jun. 29, 2017 (EP) .................................... 17178792

(51) Int. Cl.
*A61B 6/00* (2006.01)
*G06N 3/08* (2006.01)
(Continued)

(52) U.S. Cl.
CPC .......... *G06T 7/0014* (2013.01); *A61B 6/4441* (2013.01); *A61B 6/463* (2013.01);
(Continued)

(58) Field of Classification Search
None
See application file for complete search history.

(56) References Cited

U.S. PATENT DOCUMENTS 7,643,685 B2 * 1/2010 Miller ................ G06K 9/00208
 299/1.4
2009/0082660 A1 * 3/2009 Rahn ...................... A61B 6/12
 600/411
(Continued)

FOREIGN PATENT DOCUMENTS

DE 102010022791 A1 12/2011
DE 102012208850 A1 4/2013
(Continued)

OTHER PUBLICATIONS

Spiegel, M., et al. "A 2D driven 3D vessel segmentation algorithm for 3D digital subtraction angiography data." Physics in Medicine & Biology 56.19 (2011): 6401.*
(Continued)

*Primary Examiner* — Andrae S Allison
(74) *Attorney, Agent, or Firm* — Harness, Dickey & Pierce, P.L.C.

(57) ABSTRACT

A method for visualizing at least one characteristic variable of a patient in an angiographic scan via a C-arm X-ray device, an associated C-arm X-ray device and an associated computer program product are disclosed. An embodiment of the method includes acquiring at least one 2-D image of the patient via the C-arm X-ray device; determining at least one 3-D reference image by applying an image information system to the at least one 2-D image; establishing at least one characteristic variable which describes at least one vessel of the patient in the at least one 3-D reference image; and visualizing the at least one characteristic variable in the at least one 2-D image.

25 Claims, 3 Drawing Sheets

(51) Int. Cl.
*G06T 7/00* (2017.01)
*G06T 7/10* (2017.01)
*G06T 7/90* (2017.01)

(52) U.S. Cl.
CPC ............ *A61B 6/504* (2013.01); *A61B 6/5205* (2013.01); *G06N 3/08* (2013.01); *G06T 7/10* (2017.01); *G06T 7/90* (2017.01); *A61B 6/481* (2013.01); *G06T 2207/30101* (2013.01)

(56) References Cited

U.S. PATENT DOCUMENTS

| | | | | |
|---|---|---|---|---|
| 2009/0118609 | A1* | 5/2009 | Rahn | A61B 6/12 600/411 |
| 2009/0252287 | A1* | 10/2009 | Boese | A61B 6/02 378/17 |
| 2011/0026775 | A1* | 2/2011 | Waechter | G06T 7/20 382/107 |
| 2011/0096907 | A1* | 4/2011 | Mohamed | G06T 11/005 378/98 |
| 2011/0298793 | A1 | 12/2011 | Lauritsch et al. | |
| 2012/0046725 | A1* | 2/2012 | Rahn | G06F 19/00 623/1.1 |
| 2012/0238871 | A1* | 9/2012 | Pfister | A61B 6/12 600/431 |
| 2013/0076748 | A1* | 3/2013 | Rahn | G06T 19/00 345/424 |
| 2013/0202170 | A1* | 8/2013 | Blezek | G06K 9/00201 382/131 |
| 2015/0078643 | A1* | 3/2015 | John | G06T 7/0012 382/131 |
| 2015/0112182 | A1 | 4/2015 | Sharma et al. | |
| 2015/0131882 | A1* | 5/2015 | Mohr | G06T 7/174 382/131 |
| 2015/0216494 | A1 | 8/2015 | Atzinger | |
| 2016/0063726 | A1* | 3/2016 | Wenzel | G06T 7/149 382/128 |
| 2017/0270663 | A1* | 9/2017 | Hoffmann | A61B 5/02007 |
| 2018/0075221 | A1* | 3/2018 | Vergaro | G16H 15/00 |

FOREIGN PATENT DOCUMENTS

| | | |
|---|---|---|
| DE | 102014202013 A1 | 8/2015 |
| DE | 102015202082 A1 | 12/2015 |
| EP | 3128481 A1 | 2/2017 |
| WO | WO-2010041201 A1 | 4/2010 |
| WO | WO-2016145010 A1 | 9/2016 |

OTHER PUBLICATIONS

Y. Zheng, D. Liu, B. Georgescu, H. Nguyen, and D. Comaniciu, "3D deep learning for efficient and robust landmark detection in volumetric data," in International Conference on Medical Image Computing and Computer-Assisted Intervention. Springer, 2015, pp. 565-572.*

E. Nasr-Esfahani et al., "Vessel extraction in X-ray angiograms using deep learning," 2016 38th Annual International Conference of the IEEE Engineering in Medicine and Biology Society (EMBC), Orlando, FL, 2016, pp. 643-646.*

Prasoon, A., Petersen, K., Igel, C., Lauze, F., Dam, E., Nielsen, M.: Deep feature learning for knee cartilage segmentation using a triplanar convolutional neural network. In Mori, K., Sakuma, I., Sato, Y., Barillot, C., Navab, N., eds.: MICCAI 2013, Part II. vol. 8150., Springer, Heidelberg (2013) 246-253.*

Ding, Feng, Wee Kheng Leow, and Shih-Chang Wang. "Segmentation of 3D CT volume images using a single 2D atlas." International Workshop on Computer Vision for Biomedical Image Applications. Springer, Berlin, Heidelberg, 2005.*

German Search Report for European Patent No. 17178792.2 dated Jan. 17, 2018; (English Translation of Search Report).

* cited by examiner

VISUALIZATION OF AT LEAST ONE CHARACTERISTIC VARIABLE

PRIORITY STATEMENT

The present application hereby claims priority under 35 U.S.C. § 119 to European patent application number EP 17178792.2 filed Jun. 29, 2017, the entire contents of which are hereby incorporated herein by reference.

FIELD

At least one embodiment of the invention generally relates to a method for visualizing at least one characteristic variable of a patient in an angiographic scan via a C-arm X-ray device, an associated C-arm X-ray device and/or an associated computer program product.

BACKGROUND

An angiographic image which has been recorded with a C-arm angulation via a C-arm X-ray device in a cardiological catheterization laboratory typically has a two-dimensional (2D) depiction of a vessel, in particular a contrast-enhanced coronary artery. C-arm angulation describes, in particular, an angular configuration of the C-arm X-ray device. Dependent upon the contrast-enhanced coronary artery and the C-arm angulation, the angiographic image can have a vessel foreshortening and/or a vessel overlap of the contrast-enhanced coronary artery. Typically, in this event however, there is no indication that the contrast-enhanced coronary artery is imaged foreshortened or overlapped.

The vessel foreshortening and/or vessel overlap can lead to false interpretations by a user or a physician since, for example, due to the vessel foreshortening, a quantification of a vessel length or a vessel diameter of the contrast-enhanced coronary artery in the angiographic image is not possible. Therefore, for example, the vessel length of a vessel stenosis to be treated can be underestimated due to vessel foreshortening. It can result therefrom that, in the case of a stent implantation, an implant of insufficient length is selected.

Therefore, the vessel to be treated is typically captured or recorded with different C-arm angulations in order thereby to obtain a better spatial impression of the vessel to be treated. For this purpose, however, the intuition and experience of the user/physician is necessary to ensure that at least one angiographic 2-D image of all the angiographic images that have been generated with different C-arm angulations comprises the vessel to be treated without vessel foreshortening, in particular, foreshortening-free.

In DE 10 2015 202 082 A1, DE 10 2014 202 013 A1 and DE 10 2012 208 850 A1, C-arm X-ray devices are described by which angiographic scans can be carried out.

SUMMARY

At least one embodiment of the invention provides an improved method for visualizing at least one characteristic variable of a patient in an angiographic scan via a C-arm X-ray device, the associated C-arm X-ray device and an associated computer program product.

Advantageous developments are disclosed in the claims.

The inventive solution to the problem, in example embodiments, will be described below in relation to the C-arm X-ray device and also to the method for visualizing at least one characteristic variable of a patient in an angiographic scan via a C-arm X-ray device, and also to the associated computer program product and computer readable medium. Features, advantages or alternative embodiments mentioned herein are also transferable similarly to the other claimed subject matter and vice versa. In other words, the present claims (which are directed, for example, to a C-arm X-ray device) can also be further developed with the features disclosed or claimed in conjunction with a method. The corresponding functional features of the method are herein configured by way of corresponding modules from the subject matter.

At least one embodiment of the inventive method for visualizing at least one characteristic variable of a patient in an angiographic scan via a C-arm X-ray device comprises:
    providing an image information system,
    acquiring at least one 2-D image of the patient via the C-arm X-ray device,
    determining at least one 3-D reference image by applying the image information system to the at least one 2-D image,
    establishing at least one characteristic variable which describes at least one vessel of the patient in the at least one 3-D reference image, and
    visualizing the at least one characteristic variable in the at least one 2-D image.

At least one embodiment of the inventive C-arm X-ray device comprises
    a planning unit,
    a control unit, and
    a scanning unit which comprises an X-ray radiator and an X-ray detector,
the C-arm X-ray device being configured to carry out at least one embodiment of an inventive method.

At least one embodiment of the inventive computer program product is directly loadable into a memory store of a programmable computer unit and has program code segments/modules in order to carry out an inventive method when the computer program product is executed in the computer unit.

At least one embodiment of the computer program product can be a computer program or can comprise a computer program. In this way, the method according to at least one embodiment of the invention can be carried out rapidly, exactly reproducibly and robustly. The computer program product is configured such that it can carry out at least one embodiment of the inventive method steps via the computer unit. The computer unit must have the respective preconditions such as, for example, a suitable working memory store, a suitable graphics card or a suitable logic unit so that the respective method steps can be carried out efficiently.

In at least one embodiment, the computer program product is stored, for example, on a computer-readable medium or is deposited on a network or server from where it can be loaded into the processor of the computer unit which can be configured, for example, as part of the C-arm X-ray device. Furthermore, control information of the computer program product can be stored on an electronically readable data carrier. The items of control information of the electronically readable data carrier can be configured such that they carry out an inventive method when the data carrier is used in the computer unit.

Thus, the computer program product and/or computer-readable medium can also constitute the electronically readable data carrier. Examples of electronically readable data carriers are a DVD, a magnetic tape, a hard disk drive or a USB stick, on which electronically readable control information, in particular software (see above) is stored. If this control information (software) is read from the data carrier and stored in the computer unit and/or planning unit and/or scanning unit of the C-arm X-ray device, all the inventive embodiments of the above-described methods can be carried out. At least one embodiment of the invention can therefore also proceed from the aforementioned computer-readable medium and/or the aforementioned electronically readable data storage medium.

BRIEF DESCRIPTION OF THE DRAWINGS

The invention will now be described and explained in greater detail making reference to the example embodiments illustrated in the drawings, in which.

DETAILED DESCRIPTION OF THE EXAMPLE EMBODIMENTS

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "exemplary" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuity such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

At least one embodiment of the inventive method for visualizing at least one characteristic variable of a patient in an angiographic scan via a C-arm X-ray device comprises:
  providing an image information system,
  acquiring at least one 2-D image of the patient via the C-arm X-ray device,
  determining at least one 3-D reference image by applying the image information system to the at least one 2-D image,
  establishing at least one characteristic variable which describes at least one vessel of the patient in the at least one 3-D reference image, and
  visualizing the at least one characteristic variable in the at least one 2-D image.

The provision of the image information system can comprise that the image information system is set up in a clinic or in a computing center by a manufacturer of the image information system or personnel of the clinic or personnel of the computing center. The establishment or configuration of the image information system typically comprises a configuration of the image information system with suitable hardware (e.g. working memory, hard disk, input/output interfaces, monitor, input devices, storage unit, processor, etc.) and/or an installation of corresponding software, for example, an operating system and/or a computer program product for determining the at least one 3-D reference image by applying the image information system to the at least one 2-D image.

Preferably, the image information system is directly connected to the C-arm X-ray device, in particular a storage unit of the C-arm X-ray device. For this, the image information system and/or the C-arm X-ray device and/or the storage unit of the C-arm X-ray device can comprise suitable interfaces which enable, for example, an exchange, in particular, of the at least one 2-D image, of the at least one 3-D reference image and of the at least one 2-D image in which the at least one characteristic variable is visualized. The image information system can be present in the computing center and can be linked via a suitable interface to the C-arm X-ray device. Alternatively, the image information system can be configured as a component of the C-arm X-ray device.

Preferably, the acquisition of the at least one 2-D image comprises an injection of a contrast medium bolus via a contrast medium injecting device of the C-arm X-ray device. Usually, an iodine-containing contrast medium bolus is injected. Typically, a non-contrast-enhanced image is acquired before the injection of the contrast medium bolus and an angiographic image is acquired after the injection of the contrast medium bolus. The at least one 2-D image can correspond in this case to a subtraction of the non-contrastenhanced 2-D image from the angiographic 2-D image. Alternatively, the acquisition of the at least one 2-D image can entail a loading of the 2-D image, in particular, from the storage unit of the C-arm X-ray device.

The at least one 2-D image preferably includes the at least one vessel. In a preferred embodiment, the at least one 2-D image preferably includes only the at least one vessel. The at least one 2-D image can include a vessel structure of the patient, in particular a plurality of vessels of the patient.

The at least one vessel can include an arterial and/or a venous structure of a vessel structure of the patient. The at least one vessel comprises, for example, either a vessel structure or a plurality of vessels of the vessel structure. For example, the at least one vessel can be assigned to a cardiac body region. The at least one vessel can be a coronary artery (e.g. RCA=right coronary artery) and/or capillary vessels.

The at least one characteristic variable describes the at least one vessel of the patient. The at least one characteristic variable is therefore particularly relevant for example, for a user of the C-arm X-ray device or a physician, because the at least one vessel of the patient is to be examined or treated during the angiographic scan. For example, the physician performs before, during or after the angiographic scan, a surgical or interventional procedure which relates to the at least one vessel.

The application of the image information system to the at least one 2-D image normally comprises a provision of the acquired at least one 2-D image as an input parameter for the image information system. The image information system preferably has suitable device(s) for an input of the at least one 2-D image as the input parameter. The device(s) suitable therefor can comprise interfaces for a network between the image information system and the C-arm X-ray device or a DVD drive.

In particular, an image set of a plurality of 3-D images is deposited or stored in the image information system. Thus, the image information system has, in particular, device(s) for selecting and calling up the at least one 3-D reference image from the image set of the plurality of 3-D images. For example, the manufacturer of the image information system or the personnel in the hospital can have installed the image set onto the image information system. This is particularly advantageous since the patient does not have to be scanned before the angiographic scan for a recording of the at least one 3-D reference image via the C-arm X-ray device or via a computed tomography system, rather that the image set of a plurality of 3-D images, from which usually the at least one 3-D reference image is selected, typically already exists before the acquisition of the at least one 2-D image.

The image set can, alternatively or in addition to the plurality of 3-D images, comprise a 3-D model of the at least one vessel. An extended 3-D model can correspond to an idealized or modeled variant of the at least one vessel. The extended 3-D model can be formed from a plurality of different 3-D images from different patients. The plurality of 3-D images are reconstructed from scan data which has been generated, for example, via a computed tomography system.

Usually, the image set shows the heart at a particular cardiac phase and an item of information regarding the cardiac phase can be stored in a description, in particular, in a header according to the DICOM standard, of the 3-D image. Dependent upon the cardiac phase, usually the at least one vessel changes, for example in accordance with a contraction of the heart. Preferably, the image set comprises a plurality of 3-D images, each at different cardiac phases, in particular over a complete cardiac cycle. The image set can therefore have in particular 3-D image scenes or four dimensional (4-D) images, wherein the 4-D images comprise time-resolved 3-D images. The time-resolved 3-D images can be assigned in particular to at least one cardiac phase.

The image information system processes, in particular, the at least one 2-D image such that the at least one 3-D reference image is determined. The at least one 3-D reference image is preferably determined such that the greatest possible similarity or a greatest possible correlation factor exists between the at least one 2-D image and the image content of the at least one 3-D reference image. In particular, the at least one 2-D image is compared with all the 3-D images of the image set by way of the similarity analysis or the correlation. In particular, the 3-D image the image content of which has the greatest correlation factor with the at least one 2-D image is selected from the image set of the plurality of 3-D images of the image information system as the 3-D reference image.

Alternatively or additionally, in particular the at least one 2-D image with an image content of the plurality of 3-D images of the image set is registered. The determination of the at least one 3-D reference image by applying the image information system to the at least one 2-D image can include a mathematical correlation and/or a multi-dimensional interpolation and/or a loading of the at least one 3-D reference image from a memory store of the image information system. The latter is possible to the extent that the at least one 3-D reference image has already been determined at an earlier time point. The loading can, in particular, be advantageous if the determination of the at least one 3-D reference image by applying the image information system to the at least one 2-D image is computationally intensive or time-costly.

The determination of the at least one 3-D reference image by the application of the image information system to the at least one 2-D image is normally a computationally intensive process because, in particular, an N×N matrix of the at least one 2-D image is to be found in an M×M×M matrix of the plurality of 3-D images of the image set of the image information system. Normally, the at least one 2-D image is compared image for image with the plurality of 3-D images of the image set. Typically, by way of a multi-planar reconstruction from the M×M×M matrix, an M'×M' matrix is calculated since a correlation between the N×N matrix with the M'×M' matrix is less computation-intensive than a correlation of the N×N matrix with the M×M×M matrix. The multiplanar reconstruction of the M'×M' matrix typically has infinitely many solutions. Ideally, the multi-planar reconstruction is specified with a particular angle, in particular of the C-arm angulation of the C-arm X-ray device, so that the image set is restricted for the correlation or the similarity analysis or the registration.

Advantageously, the determination of the at least one 3-D reference image by the application of the image information system to the at least one 2-D image is unambiguous. This means, in other words, that for exactly one input, there exists exactly one result in the image information system.

Typically, the determination of the at least one 3-D reference image by the application of the image information system to the at least one 2-D image is faster, more exact and/or more unambiguous the more image information the at least one 2-D image has. The image information can correspond to an image content of the at least one 2-D image and/or description parameters that are present in the header of the at least one 2-D image. The more of the image information that is present, the smaller in particular is the image set for the correlation or the similarity analysis. The smaller the image set, in particular, the faster the at least one 3-D reference image is determined. The correlation or the similarity can be improved by additional boundary conditions which result from the at least one 2-D image.

The establishment of the at least one characteristic variable preferably comprises applying an algorithm which is preferably configured such that the at least one characteristic variable which the acquired at least one 2-D image does not have, can be established from the 3-D reference image. The at least one characteristic variable preferably comprises pictorial depth information of the at least one 3-D reference image which the at least one 2-D image does not directly possess.

The at least one characteristic variable is preferably visualized in the at least one 2-D image in that the at least one 2-D image comprises at least a part of the pictorial depth information of the at least one 3-D reference image. By this, the at least one 2-D image can have a spatial impression.

One embodiment provides that the at least one characteristic variable describes a vessel foreshortening of the at least one vessel. The at least one characteristic variable can be a measure for a severity of the vessel foreshortening or for a probability of an occurrence of the vessel foreshortening. In this case, the at least one characteristic variable preferably has information about the extent to which the at least one vessel is represented foreshortened in the at least one 2-D image. Preferably, the vessel foreshortening is characterized the more markedly by the at least one characteristic variable, the more foreshortened the at least one vessel is represented in the at least one 2-D image.

One embodiment provides that the at least one characteristic variable describes a vessel overlap of the at least one vessel. In this case, the at least one characteristic variable preferably has information about the extent to which the at least one vessel is represented overlapped by another vessel and/or by a part of the at least one vessel, in particular partially, in the at least one 2-D image.

One embodiment provides that at least one metaparameter is assigned to the at least one 2-D image, wherein the at least one metaparameter is used in determining the at least one 3-D reference image and the at least one metaparameter comprises at least one parameter of the following list:
 an item of metainformation regarding the acquisition of the at least one 2-D image via the C-arm X-ray device,
 a vessel designation of the at least one vessel, and
 a cardiac phase of the patient.

In principle it is conceivable that the metainformation regarding the acquisition of the at least one 2-D image via the C-arm X-ray device and/or the cardiac phase of the patient is automatically assigned to the 2-D image, in particular in the header of the at least one 2-D image. The metainformation comprises, in particular, a configuration of the C-arm X-ray device during the angiographic scan and is acquired online, in particular in real time, and assigned to the at least 2-D image.

The cardiac phase of the patient is acquired, for example, with an echocardiograph online in real time, in particular during the angiographic scan, wherein the echocardiograph is connected via an interface to the C-arm X-ray device. The cardiac phase is assigned to the at least one 2-D image, in particular in the header of the at least one 2-D image. Taking account of the cardiac phase, the determination of the at least one 3-D reference image can be improved in that in particular in the image set for the similarity analysis, only those 3-D images with the exact or at least a similar cardiac phase of the at least one 2-D image remain. In principle, it is also conceivable that the at least one 2-D image is selected according to the cardiac phase and accordingly the at least one 3-D reference image is determined. Furthermore, the at least one 2-D image can comprise a plurality of cardiac phases, so that by the application of the image information system to the at least one 2-D image with a plurality of cardiac phases, the at least one 3-D reference image is determined with a plurality of cardiac phases. The plurality of cardiac phases can, in particular, form a cardiac cycle.

Furthermore, the at least one metaparameter can have the vessel designation of the at least one vessel, for example, RCA. The vessel designation of the at least one vessel can preferably be assigned by a user on a monitor of the C-arm X-ray device to the at least one 2-D image, wherein the metaparameter is stored, in particular, in the header of the at least one 2-D image. The user can interact on the monitor of the C-arm X-ray device with a graphical user interface. Usually, the C-arm X-ray device has for this purpose an input device, for example, a mouse or a keyboard. Alternatively or additionally, it is conceivable that by way of landmark recognition, the vessel designation is automatically assigned to the at least one 2-D image. Taking account of the vessel designation, the determination of the at least one 3-D reference image can be improved in that the image set of the 3-D images of the image information system is restricted to those 3-D images which the vessel has with the appropriate vessel designation. For example, only those 3-D images are taken into account to which a vessel with the vessel designation of the at least one vessel is assigned.

One embodiment provides that the at least one metaparameter comprises the vessel designation of the at least one vessel and wherein the vessel designation comprises at least one parameter of the following list:
 a vessel diameter of the at least one vessel,
 a maximum curvature of the at least one vessel, and
 a length of the at least one vessel.

The vessel diameter, the maximum curvature and the length of the at least one vessel can be assigned to a group of parameters which has semantic information regarding the vessel. The at least one vessel is described or identified in this case with descriptive features. The determination of the at least one 3-D reference image by the application of the image information system to the at least one 2-D image can take place according to the descriptive features. The vessel diameter, the maximum curvature and/or the length of the at least one vessel can be acquired, for example, by the user or automatically in the at least one 2-D image. The vessel diameter, the maximum curvature and/or the length of the at least one vessel can be selected, in particular from specialist medical literature or according to standard values or, in particular, formed from metrics which have been trained with a plurality of training vessels. Preferably the respective descriptive features of the image content of the 3-D images are assigned to the 3-D images of the image set, so that by the application of the image information system to the at least one 2-D image according to the descriptive features, in particular, the image set is restricted.

One embodiment provides that the at least one metaparameter has the metainformation regarding the acquisition of the at least one 2-D image via the C-arm X-ray device and wherein the metainformation comprises at least one parameter of the following list:
 a spatial position of the C-arm X-ray device,
 a spacing between an X-ray radiator of the C-arm X-ray device and an X-ray detector of the C-arm X-ray device, and
 a spatial position of the patient table.

The C-arm X-ray device preferably has at least one coordinate system for specifying the spatial position of the C-arm X-ray device and the spatial position of the patient table. The spatial position of the C-arm X-ray device has, in particular, a position in the at least one coordinate system, an orientation of the C-arm X-ray device and a configuration for the position and the orientation. In addition, the spatial position of the C-arm X-ray device can have the configuration as to how the position of the C-arm X-ray device and the orientation of the C-arm X-ray device has been achieved, for example, by way of a movement in or out of a telescopic unit of the C-arm X-ray device or by a turning of a rotation joint of the C-arm X-ray device.

By way of the spatial position of the C-arm X-ray device, in particular, a C-arm angulation can be established, wherein the C-arm angulation is relevant in particular for the determination of the at least one 3-D reference image by the application of the image information system to the at least one 2-D image, since through the stipulation of the C-arm angulation, the angle for the multi-planar reconstruction is specified, by which the determination of the at least one 3-D reference image is significantly accelerated. By way of the stipulation of the C-arm angulation, the image set of the 3-D images is restricted since only the 3-D images to which the C-arm angulation is assigned can be selected. For example, the spatial position has a positional angle of the C-arm X-ray device and an orbital angle of the C-arm X-ray device, in particular the C-arm angulation of the C-arm X-ray device.

The spacing between the X-ray radiator and the X-ray detector typically provides a measure for the scaling of the at least one 2-D image. In the optical representation, the measure for the scaling is typically named the zoom or zoom factor. Preferably, on determination of the reference 3-D image, the more 3-D images that are taken into account with relatively small vessels, the smaller is the spacing between the X-ray radiator and the X-ray detector.

By way of the at least one metaparameter, the image set of the 3-D images, the scope of which usually scales directly with a computational complexity of the determination of the at least one 3-D reference image can advantageously be restricted. In particular, it is conceivable that for the at least one metaparameter, a tolerance range is specified. The tolerance range describes, in particular, a boundary condition for the similarity analysis or the correlation or the registration. The smaller the tolerance range is, the more restricted is the image set.

The determination of the at least one 3-D reference image by the application of the image information system to the at least one 2-D image can comprise a modification of the at least one 2-D image by a movement field. The movement field corresponds, in particular, to a mathematical operation according to which the at least one 2-D image is amended. For example, the movement field can have a cardiac phase transformation. By way of the modification of the at least one 2-D image of a first cardiac phase by way of the movement field, based, for example, on the at least one 2-D image, a further 2-D image can be calculated in a second cardiac phase. By way of the modification in accordance with the movement field, the at least one 2-D image can therefore be simulated at different cardiac phases. The 3-D images of the image set can usually be adapted in accordance with the movement field, so that in particular a higher correlation factor is found than if the 3-D images are not adapted.

It is further conceivable that via suitable sensors, in particular a camera or a chest belt, a breathing movement of the patient is acquired. In accordance with the breathing movement of the patient, the movement field can be calculated, wherein the at least one 2-D image is modified by the movement field. The movement field can be calculated both in accordance with the breathing movement of the patient and also in accordance with the cardiac phase of the patient.

One embodiment provides that the determination of the at least one 3-D reference image by the application of the image information system to the at least one 2-D image comprises:
  segmenting the at least one 2-D image according to the at least one vessel, and
  applying the image information system to the at least one segmented 2-D image.

By way of the segmentation of the at least one 2-D image according to the at least one vessel, preferably a region of the at least one 2-D image in which the visualizing of the at least one characteristic variable is particularly useful can be emphasized. Usually, the at least one characteristic variable can be visualized only according to the at least one vessel. The region without the at least one vessel is usually of little or no interest to the user.

In particular, the gray scale-based or model-based segmentation of the at least one 2-D image can be carried out manually semi-automatically or entirely automatically. If the at least one 2-D image is segmented according to the at least one vessel, there remains in the at least one 2-D image information relevant, in particular, solely for the determination of the at least one 3-D reference image. For example, the at least one vessel can be imaged in a midline. The segmentation can result in a binary mask of the at least one 2-D image. Alternatively or additionally, a contour of the at least one vessel can be established by way of the segmentation.

In principle, it is conceivable that the plurality of 3-D images of the image set are segmented before the determination of the at least one 3-D reference image similarly to the at least one 2-D image. In particular only the segmented image content enters the determination of the at least one 3-D reference image. In a preferred embodiment, by the application of the image information system to the at least one segmented 2-D image, the 3-D reference image is determined faster than by way of the application of the image information system to the 2-D image without prior segmentation. This effect usually takes place in that through the segmentation of the at least one 2-D image, less irrelevant image content of the segmented 2-D image is correlated or registered with the 3-D images of the image set. Advantageously, the correlation or the similarity analysis or the registration is faster the less irrelevant image content, for example background, the segmented 2-D image has.

One embodiment provides that the determination of the at least one 3-D reference image by the application of the image information system to the at least one 2-D image comprises an establishment of a 2-D reference image, the 2-D reference image being assigned to the at least one 3-D reference image.

The image information system can comprise, in particular, a further 2-D image set of 2-D images wherein the at least one 2-D reference image is determined from the further 2-D image set. The establishment of the 2-D reference image preferably takes place automatically by the application of the image information system to the at least one 2-D image, in particular according to the same algorithms that are used for determining the at least one 3-D reference image by the application of the image information system to the at least one 2-D image. In particular, the mathematical methods such as correlation, registration and similarity analyses are used.

Alternatively, it is conceivable that the C-arm X-ray device has suitable device(s) for establishing the 2-D reference image and the C-arm X-ray device provides the 2-D reference image as the input parameter of the image information system.

Normally, following the establishment of the 2-D reference image, the at least one 3-D reference image assigned to the 2-D reference image is determined as the output of the image information system. Usually, the 2-D reference image is already assigned to the at least one 3-D reference image. Alternatively, the assignment of the 2-D reference image to the at least one 3-D reference image can take place similarly to the determination of the at least one 3-D reference image by the application of the image information system to the at least one 2-D image. In particular, the mathematical methods such as correlation, registration and similarity analyses are used. In rare cases, the assignment of the 2-D reference image to the at least one 3-D reference image by the user can take place through interaction with the graphical user interface.

The 2-D reference image preferably has at least one part of the metaparameters of the at least one 2-D image. For example, the 2-D reference image can be provided via the C-arm X-ray device at an earlier time point in an identical or similar configuration of the C-arm X-ray device and provided to the image information system. In this case, the 2-D reference image has, for example, the same spatial position of the C-arm X-ray device as during the acquisition of the at least one 2-D image. Alternatively, it is conceivable that the 2-D reference image has been calculated from the 3-D reference image, for example, via the multi-planar reconstruction.

One embodiment provides that the visualization of the at least one characteristic variable in the at least one 2-D image comprises:
  segmenting the at least one 2-D image according to the at least one vessel, and
  masking the at least one characteristic variable in the at least one segmented 2-D image.

Preferably, the at least one characteristic variable is masked in the at least one segmented 2-D image according to the at least one vessel. The masking of the at least one characteristic variable in the at least one segmented 2-D image can preferably emphasize the at least one vessel visually. The region without the at least one vessel is usually of little or no interest to the user and is removed by the masking.

One embodiment provides that the at least one characteristic variable is visualized color-coded in the at least one 2-D image. If the at least one characteristic variable is established in the 3-D reference image, for example, the at least one characteristic variable is color-coded in the 3-D reference image and the color-coding of the at least one characteristic variable is transferred or projected from the 3-D reference image onto the 2-D reference image.

The color-coding of the at least one characteristic variable can represent the at least one vessel in a first color, for example, green if the at least one characteristic variable is relatively low, or in a second color, for example red if the at least one characteristic variable is relatively high. The measure for the severity of the vessel foreshortening is established, for example, with an angle between the midline of the at least one vessel and a visualization plane of the at least one 2-D image in an interval of 0-90°. The at least one characteristic variable is visualized, for example, more in the first color if the angle is closer to 0° and more in the second color if the angle is closer to 90°. Usually, the at least one characteristic variable is visualized more in the first color the less the vessel foreshortening is. In contrast, the at least one characteristic variable is visualized more in the second color the greater the vessel foreshortening is.

The color-coding of the at least one characteristic variable according to the at least one 3-D reference image can also be stored in the image information system. The establishment of the at least one characteristic variable and/or the visualization of the at least one characteristic variable can therefore correspond to a loading of the color-coding of the at least one characteristic variable according to the at least one 3-D reference image from a memory store of the image information system.

One embodiment provides that the visualization of the at least one characteristic variable in the at least one 2-D image comprises a projection of the at least one characteristic variable onto the at least one 2-D image.

The projection of the at least one characteristic variable usually takes place along a projection direction from the at least one 3-D reference image onto the at least one 2-D image. Usually, a distinction is made between a parallel projection and a perspective projection. In the parallel projection, the at least one characteristic variable established in the at least one 3-D reference image is averaged along the projection direction and transferred to the at least one 2-D image. The parallel projection is an idealization since the at least one 2-D image usually has a perspective depiction of the at least one vessel, in particular the vessel structure or the anatomy. The perspective projection of the at least one characteristic variable typically requires a prior registration with optional transformation of the at least one 2-D image according to the at least one 3-D reference image.

One embodiment provides that the at least one characteristic variable of a control unit of the C-arm X-ray device is provided which according to the at least one characteristic variable establishes control commands and wherein the control unit moves the C-arm X-ray device in accordance with the control commands at least through an angle and the C-arm X-ray device acquires a further 2-D image in accordance with the control commands.

Preferably, following the establishment of the at least one characteristic variable in the at least one 3-D reference image, the at least one 2-D image in which the at least one characteristic variable has been visualized is provided to the C-arm X-ray device for the acquisition of the further 2-D image. Alternatively, it is conceivable that the established at least one characteristic variable is provided to the C-arm X-ray device before the visualization. Preferably, in the further 2-D image, the at least one vessel is acquired, in particular, without vessel foreshortening. The at least one vessel can correspond to the vessel, for example, a coronary artery to be treated, which is to be acquired in the further 2-D image, or alternatively, another vessel which is already imaged in the at least one 2-D image.

The control commands specify, in particular, the at least one angle, in particular the orbital angle and/or the positional angle, of the C-arm X-ray device. In other words, the control commands specify the C-arm angulation. The control unit can move the C-arm X-ray device in accordance with the control commands. Preferably, following the movement of the C-arm X-ray device through the at least one angle, in particular through the orbital angle and/or the positional angle, scan data can be generated from which the further 2-D image can be reconstructed. From the at least one 2-D image and the further 2-D image, alternatively or additionally, a 3-D image can be reconstructed.

One embodiment provides that the image information system comprises an atlas, the atlas comprising at least one depiction of the at least one 3-D reference image and wherein by an application of the atlas to the at least one 2-D image, the at least one 3-D reference image is determined.

The image information system, in particular the atlas, typically has the image set of a plurality of 3-D images and the further 2-D image set of a plurality of 2-D images from different patients or according to different models. The image set and the further 2-D image set can comprise, for example, a variant of the at least one vessel changed by way of a movement field. Alternatively, the image set and the further 2-D image set can also comprise variants of the at least one vessel which have been calculated at different cardiac phases or respiratory phases or calculated by way of algorithms. Preferably, the individual 2-D images are already assigned to the 3-D images. The atlas is preferably configured such that by way of an application of the atlas to the at least one 2-D image, firstly the 2-D image of the 2-D image set with the greatest similarity is selected and the 3-D image assigned to that 2-D image is determined as the at least one 3-D reference image.

One embodiment provides that the image information system comprises an artificial neural network, the neural network being trained for determining the at least one 3-D reference image through the application of the artificial neural network to the at least one 2-D image and wherein by an application of the artificial neural network to the at least one 2-D image, the at least one 3-D reference image is determined.

An artificial neural network (ANN) is, in particular, a network of artificial neurons simulated in a computation program. The artificial neural network is herein typically based on a networking of a plurality of artificial neurons. The artificial neurons are typically arranged on different layers. Usually, the artificial neural network comprises an input layer and an output layer the neuron output of which is visible as the only neuron output of the artificial neural network. Layers arranged between the input layer and the output layer are typically designated hidden layers. Typically, an architecture and/or topology of an artificial neural network is firstly initiated and then, in a training phase is trained for a special task or for a plurality of tasks. The training of the artificial neural network herein typically comprises a changing of a weighting of a connection between two artificial neurons of the artificial neural network. The training of the artificial neural network can also comprise a development of new connections between artificial neurons, a removal of existing connections between artificial neurons, an adaptation of threshold values of the artificial neurons and/or an addition or a removal of artificial neurons. Two differently trained artificial neural networks can thus carry out different tasks, although they have, for example, the same architecture and/or topology.

It is now proposed that a trained artificial neural network configured in this way is selected wherein by the application of the trained artificial neural network to the at least one 2-D image enables a determination of the at least one 3-D reference image. The artificial neural network can, in particular, have been trained with the image set of a plurality of 3-D images and with the further 2-D image set of a plurality of 2-D images. The trained artificial neural network can be suitable only for determining the at least one 3-D reference image by the application of the trained artificial neural network to the at least one 2-D image. Alternatively, it can also fulfill other tasks. It can arise that different artificial neural networks are established which can similarly carry out the determination of the at least one 3-D reference image.

At least one embodiment of the inventive C-arm X-ray device comprises
 a planning unit,
 a control unit, and
 a scanning unit which comprises an X-ray radiator and an X-ray detector,
the C-arm X-ray device being configured to carry out at least one embodiment of an inventive method.

The planning unit can have the monitor with the graphical user interface and the input device. Usually, the user can interact with the planning unit, in particular via the input device. For example, C-arm X-ray device scan data and/or the at least one 2-D image and/or the at least one 3-D reference image can be displayed to the user on the monitor. The planning unit can display on the monitor, in particular, the at least one 2-D image in which the at least one characteristic variable is visualized.

The control unit has in particular a programmable computer unit. In particular the control unit or the planning unit can comprise the image information system.

The scanning unit comprises, in particular, a support apparatus for the X-ray radiator and the X-ray detector. Usually, the support apparatus can have at least one support element, at least one rotation joint and/or at least one telescope unit. Preferably, the X-ray radiator and the X-ray detector are arranged on a C-arm which is part of the support apparatus. The C-arm X-ray device can preferably have different spatial positions and can approach the different spatial positions automatically in accordance with suitable control commands. The control commands are preferably provided by the control unit. Usually, the support apparatus can have device(s) so that the X-ray radiator and the X-ray detector can be moved according to the orbital angle or the positional angle and that the spacing between the X-ray radiator and the X-ray detector can be changed.

At least one embodiment of the inventive computer program product is directly loadable into a memory store of a programmable computer unit and has program code segments/modules in order to carry out at least one embodiment of an inventive method when the computer program product is executed in the computer unit.

At least one embodiment of the computer program product can be a computer program or can comprise a computer program. In this way, the method according to at least one embodiment of the invention can be carried out rapidly, exactly reproducibly and robustly. The computer program product is configured such that it can carry out at least one embodiment of the inventive method steps via the computer unit. The computer unit must have the respective preconditions such as, for example, a suitable working memory store, a suitable graphics card or a suitable logic unit so that the respective method steps can be carried out efficiently.

In at least one embodiment, the computer program product is stored, for example, on a computer-readable medium or is deposited on a network or server from where it can be loaded into the processor of the computer unit which can be configured, for example, as part of the C-arm X-ray device. Furthermore, control information of the computer program product can be stored on an electronically readable data carrier. The items of control information of the electronically readable data carrier can be configured such that they carry out at least one embodiment of an inventive method when the data carrier is used in the computer unit.

Thus, the computer program product and/or computer-readable medium can also constitute the electronically readable data carrier. Examples of electronically readable data carriers are a DVD, a magnetic tape, a hard disk drive or a USB stick, on which electronically readable control information, in particular software (see above) is stored. If this control information (software) is read from the data carrier and stored in the computer unit and/or planning unit and/or scanning unit of the C-arm X-ray device, all the inventive embodiments of the above-described methods can be carried out. At least one embodiment of the invention can therefore also proceed from the aforementioned computer-readable medium and/or the aforementioned electronically readable data storage medium.

Figure 1:
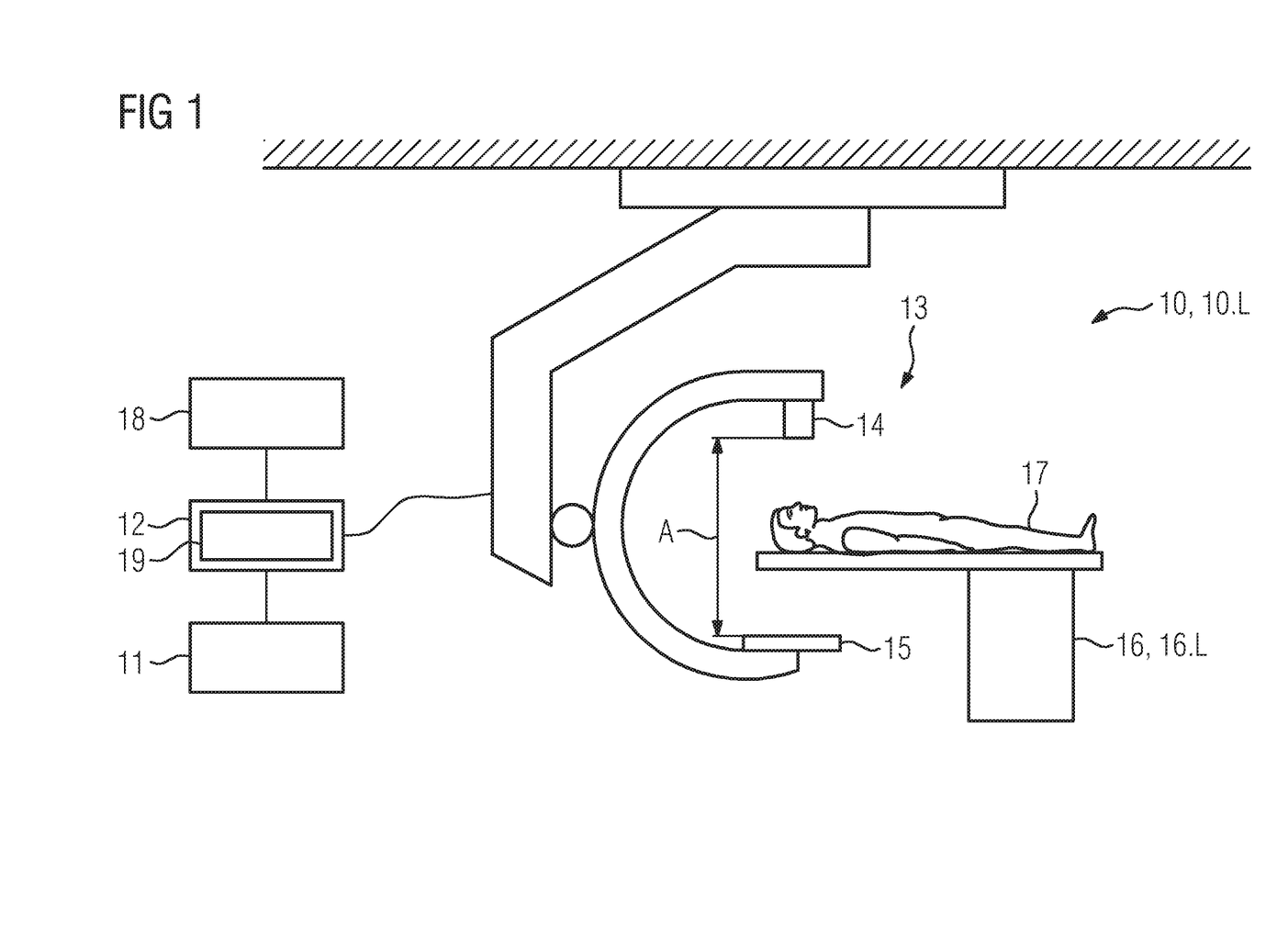
FIG. 1 shows an example embodiment of an inventive C-arm X-ray device.

FIG. 1 shows an inventive C-arm X-ray device 10 which comprises a planning unit 11, a control unit 12 and a scanning unit 13. The scanning unit 13 comprises an X-ray radiator 14 and an X-ray detector 15. The control unit 12 has, in particular, a programmable computer unit 19. The patient 17 is arranged on a patient table 16 which is height-adjustable and is also movable in two spatial directions. In the case shown, the image information system 18 is configured as part of the C-arm X-ray device 10. Alternatively, it is also conceivable that the image information system 18 is provided in a computing center and is connected via a suitable interface to the C-arm X-ray device 10. In this case, a system consisting of the image information system 18 and the X-ray device 10 is claimed.

The image information system 18 is connected, with regard to a data exchange, to the control unit 12, in particular the programmable computer unit 19.

The image information system 18 comprises an atlas wherein the atlas has at least one depiction of the at least one 3-D reference image and wherein by an application of the atlas to the at least one 2-D image, the at least one 3-D reference image is determined.

According to an alternative embodiment (not shown), the image information system 18 comprises an artificial neural network, the neural network being trained for determining the at least one 3-D reference image through the application of the artificial neural network to the at least one 2-D image and wherein by an application of the artificial neural network to the at least one 2-D image, the at least one 3-D reference image is determined.

Figure 2:
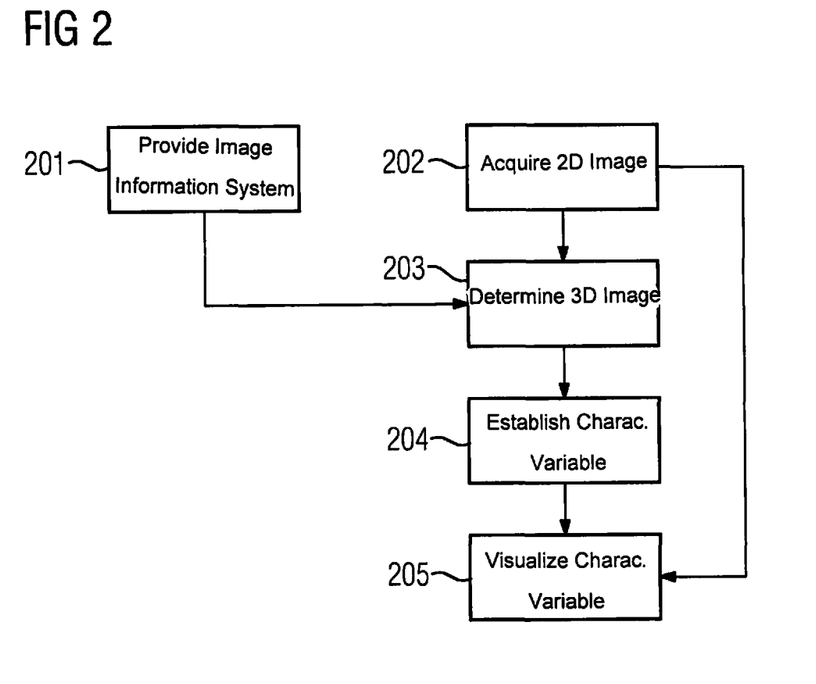
FIG. 2 shows a flow diagram of an example embodiment of an inventive method.
Figure 3:
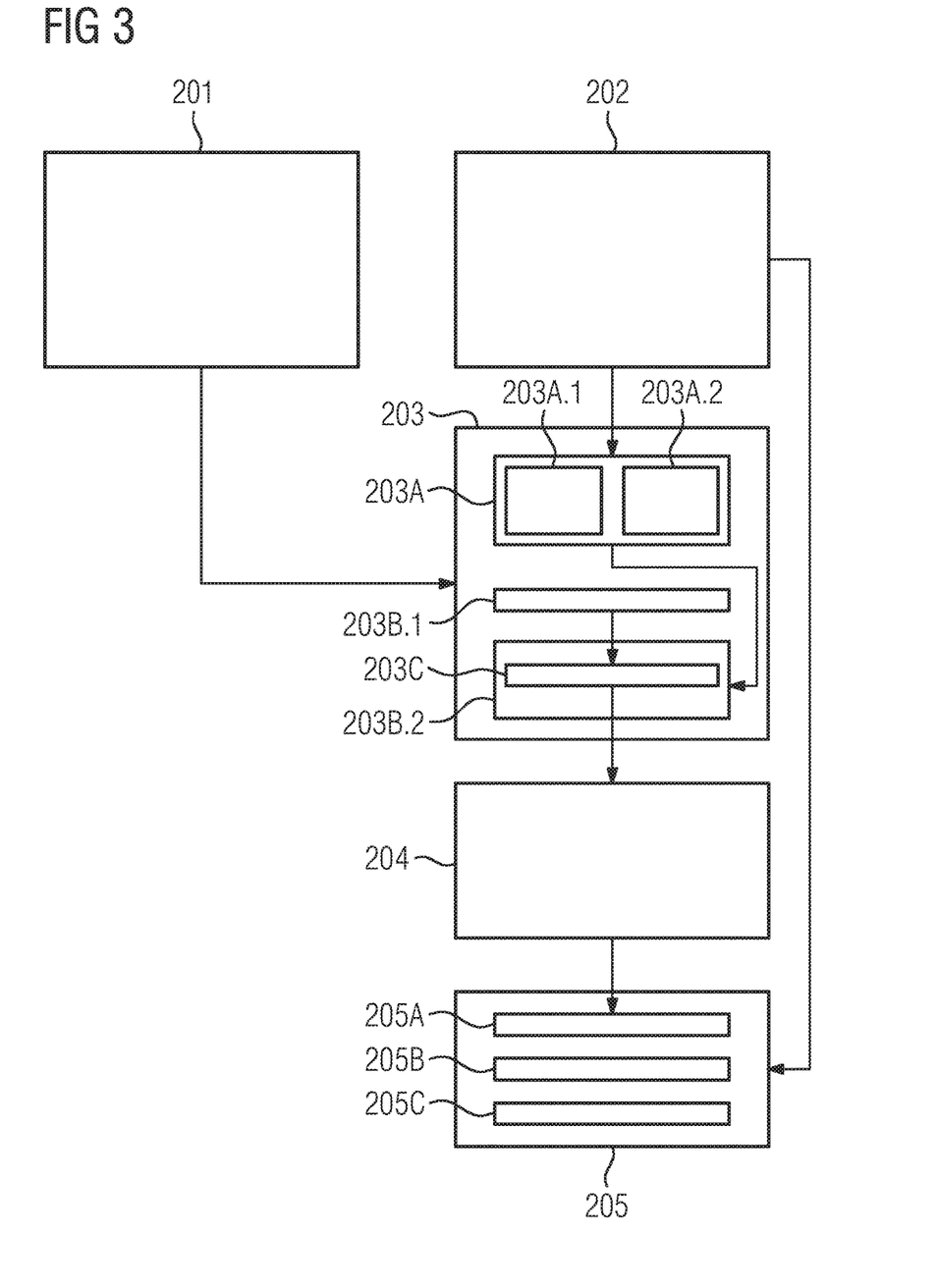
FIG. 3 shows an embodiment of the inventive method.

The C-arm X-ray device 10 is configured, in particular with the planning unit 11, the control unit 12 and the scanning unit 13, to carry out a method according to FIG. 2 or FIG. 3.

FIG. 2 shows a flow diagram of the inventive method for visualizing at least one characteristic variable of the patent 17 in an angiographic scan via the C-arm X-ray device 10. The inventive method comprises the method steps 201-205.

The method step 201 denotes the provision of an image information system 18.

The method step 202 denotes the acquisition of at least one 2-D image of the patient 17 via the C-arm X-ray device 10.

The method step 203 denotes the determination of at least one 3-D reference image by applying the image information system 18 to the at least one 2-D image.

The method step 204 denotes the establishment of at least one characteristic variable which describes at least one vessel of the patient 17 in the at least one 3-D reference image.

The method step 205 denotes the visualization of the at least one characteristic variable in the at least one 2-D image.

For example, the C-arm X-ray device can display the at least one 2-D image in which the at least one characteristic variable has been visualized, on a monitor of the planning unit 11. Alternatively or additionally, the image information system 18 can have a further monitor on which the at least one 2-D image in which the at least one characteristic variable has been visualized can be displayed.

FIG. 3 shows a flow diagram of an embodiment of the inventive method for visualizing at least one characteristic variable of the patent 17 in an angiographic scan via the C-arm X-ray device 10.

The following description is essentially restricted to the differences from the example embodiment in FIG. 2 wherein, with regard to method steps which remain the same, reference is made to the description of the example embodiment in FIG. 2. Method steps which are substantially the same are, on principle, identified with the same reference signs.

The at least one characteristic variable describes a vessel foreshortening of the at least one vessel. Alternatively or additionally, the at least one characteristic variable can describe a vessel overlap of the at least one vessel.

The method step 203A denotes that at least one metaparameter is assigned to the at least one 2-D image, wherein the at least one metaparameter is used in determining the at least one 3-D reference image and the at least one metaparameter comprises at least one parameter of the following list:

an item of metainformation regarding the acquisition of the at least one 2-D image via the C-arm X-ray device, a vessel designation of the at least one vessel, and a cardiac phase of the patient 17.

The method step 203A.1 denotes that the at least one metaparameter comprises the metainformation regarding the acquisition of the at least one 2-D image via the C-arm X-ray device 10 and that the metainformation comprises at least one parameter of the following list:

a spatial position 10.L of the C-arm X-ray device 10, a spacing A between an X-ray radiator 14 of the C-arm X-ray device 10 and an X-ray detector 15 of the C-arm X-ray device 10, and a spatial position 16.L of the patient table 16.

The spatial position 10.L, the spacing A and the spatial position 16.L can each be placed in relation to one another via suitable transformations, in particular coordinate transformations. For example, the at least one 2-D image and/or the at least one 3-D reference image can comprise the spatial position 10.L, the spacing A and the spatial position 16.L as part of the respective header.

The method step 203A.2 denotes that the at least one metaparameter has the vessel designation of the at least one vessel and that the vessel designation comprises at least one parameter of the following list:

a vessel diameter of the at least one vessel, a maximum curvature of the at least one vessel, and a length of the at least one vessel.

The method step 203B.1 denotes that the determination of the at least one 3-D reference image by the application of the image information system 18 to the at least one 2-D image comprises a segmentation of the at least one 2-D image according to the at least one vessel.

The method step 203B.2 denotes that the determination of the at least one 3-D reference image by the application of the image information system 18 to the at least one 2-D image comprises an application of the image information system 18 to the at least one segmented 2-D image.

The at least one segmented 2-D image from the method step 203B.1 and the at least one metaparameter from the method step 203A enter into the method step 203B.2.

The method step 203C denotes that the determination of the at least one 3-D reference image by the application of the image information system 18 to the at least one 2-D image comprises the establishment of a 2-D reference image assigned to the at least one 2-D image, the 2-D reference image being assigned to the at least one 3-D reference image.

In principle, it is conceivable that the method steps 203, 203A, 203A.1, 203A.2, 203B.1, 203B.2 and 203C are carried out only separately from one another or in any desired combination of these method steps.

The method step 205A denotes that the at least one characteristic variable is visualized color-coded in the at least one 2-D image. The color-coding in the RGB color space (RGB=red, green, blue) can be calculated, for example, as follows:

$$Red=\cos(90°-alpha)$$

$$Green=1-red$$

$$Blue=0$$

The parameters red, green and blue indicate the respective color proportions. The parameter alpha corresponds to an angle between the at least one vessel, in particular a midline of the at least one vessel and the visualization plane of the at least one 2-D image in the interval 0-90°.

A further alternative formula for color-coding is as follows:

$$Red=\sqrt{Normalizationvalue}$$

$$Green=1-red$$

$$Blue=0$$

The normalization value is calculated according to the absolute angle of the midline without any sign, for example, the normalization angle is 0 if the absolute angle is 0° and the normalization value is 1 if the absolute angle is 90°.

The method step 205B denotes that the visualization of the at least one characteristic variable in the at least one 2-D image comprises a projection of the at least one characteristic variable onto the at least one 2-D image.

The method step 205C denotes that the visualization of the at least one characteristic variable in the at least one 2-D image comprises:
  segmenting the at least one 2-D image according to the at least one vessel, and
  masking the at least one characteristic variable in the at least one segmented 2-D image.

In particular, the method steps 204 and 205 and the subordinate method steps 205A, 205B and 205C can be carried out both via the C-arm X-ray device 10 and also via the image information system 18. A separate performance of the aforementioned method steps is conceivable if the image information system 18 is present, for example, in a computing center outside a hospital, whereas the C-arm X-ray device is situated in the hospital.

According to a first variant embodiment, the method steps 204 and 205 and the subordinate method steps 205A, 205B and 205C are carried out via the C-arm X-ray device 10.

According to a second variant embodiment, the method step 204 is carried out via the image information system 18 and the method step 205, as well as the subordinate method steps 205A, 205B and 205C are carried out via the C-arm X-ray device 10.

According to a third variant embodiment, the method steps 204 and 205 and the subordinate method steps 205A, 205B and 205C are carried out by the image information system 18.

In an alternative embodiment (not shown) the method steps 205A, 205B and 205C can be combined as desired and also carried out separately from one another.

If relevant, further possibilities beyond the three variants set forth here for an inventive execution of the method are known to a person skilled in the art although for reasons of clarity, these are not described here.

The C-arm X-ray device 10 and the image information system 18 therefore have, in particular, device(s) for transmitting, receiving and displaying the at least one 2-D image, the at least one 3-D reference image, the 2-D reference image and/or the at least one 2-D image in which the at least one characteristic variable has been visualized. Preferably, the transmission, reception and/or display take place automatically.

The at least one 2-D image, the at least one 3-D reference image, the 2-D reference image and/or the at least one 2-D image in which the at least one characteristic variable has been visualized can be stored in a suitable format and/or transferred according to a suitable network protocol.

According to a further embodiment, the at least one characteristic variable of a control unit 12 of the C-arm X-ray device 10 is provided which according to the at least one characteristic variable establishes control commands and the control unit 12 moves the C-arm X-ray device 10 in accordance with the control commands at least through an angle and the C-arm X-ray device 10 acquires a further 2-D image according to the control commands.

The method steps of at least one embodiment of the inventive method shown in FIGS. 2 and 3 are carried out by the computer unit 19 of the C-arm X-ray device 10. For this purpose, the computer unit 19 comprises required software and/or computer programs and/or a computer program product which are stored in a storage unit of the computer unit 19. The software and/or the computer programs and/or the computer program product comprise program segments/modules which are configured to carry out the method steps described when the computer program and/or the software and/or the computer program product is executed in the computer unit 19 via a processor unit of the computer unit 19.

Although the invention has been illustrated and described in detail with the preferred example embodiment, the invention is not restricted by the examples disclosed. Variations thereof can be derived by a person skilled in the art without departing from the scope of protection of the invention as defined by the following claims.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for visualizing at least one characteristic variable of a patient in an angiographic scan via a C-arm X-ray device, the method comprising:
   providing an image information system having a plurality of stored reference images of different patients;
   acquiring at least one 2-D image of the patient via the C-arm X-ray device;
   determining at least one best fit 3-D reference image from the plurality of stored 3-D reference images from the image information system, wherein the at least one 2-D image is provided as an input parameter for the image information system;
   establishing at least one characteristic variable which describes at least one vessel of the patient in the at least one 3-D reference image, wherein the at least one characteristic variable describes at least one of a vessel foreshortening of the at least one vessel or a vessel overlap of the at least one vessel; and
   displaying the at least one characteristic variable in the at least one 2-D image.

2. The method of claim 1, wherein at least one metaparameter is assigned to the at least one 2-D image, wherein the at least one metaparameter is used in determining the at least one 3-D reference image and wherein the at least one metaparameter comprises at least one parameter of:
   an item of metainformation regarding the acquiring of the at least one 2-D image via the C-arm X-ray device,
   a vessel designation of the at least one vessel, and
   a cardiac phase of the patient.

3. The method of claim 2, wherein the at least one metaparameter comprises the metainformation regarding the acquiring of the at least one 2-D image via the C-arm X-ray device and wherein the metainformation comprises at least one parameter of:
   a spatial position of the C-arm X-ray device,
   a spacing between an X-ray radiator of the C-arm X-ray device and an X-ray detector of the C-arm X-ray device, and
   a spatial position of a table of the patient.

4. A C-arm X-ray device, comprising:
   an image information system having at least one of a plurality reference images of different patients or a 3-D model;
   a planning unit;
   a control unit; and
   a scanning unit which includes an X-ray radiator and an X-ray detector, wherein the C-arm X-ray device is configured to carry out at least:
   acquiring at least one 2-D image of a patient via the C-arm X-ray device;
   determining at least one best fit 3-D reference image from a plurality 3-D reference images of different patients stored in the image information system, wherein the at least one 2-D image is provided as an input parameter for the image information system;
   establishing at least one characteristic variable which describes at least one vessel of the patient in the at least one 3-D reference image, wherein the at least one characteristic variable describes at least one of a vessel foreshortening of the at least one vessel or a vessel overlap of the at least one vessel; and
   visualizing the at least one characteristic variable in the at least one 2-D image.

5. The method of claim 2, wherein the at least one metaparameter comprises the vessel designation of the at least one vessel and the vessel designation comprising at least one parameter of:
   a vessel diameter of the at least one vessel,
   a maximum curvature of the at least one vessel, and
   a length of the at least one vessel.

6. The method of claim 1, wherein the determining of the at least one 3-D reference image by applying of the image information system to the at least one 2-D image comprises:
   segmenting the at least one 2-D image according to the at least one vessel, and
   applying the image information system to the at least one 2-D image after the segmenting.

7. The method of claim 1, wherein the determining of the at least one 3-D reference image by applying of the image information system to the at least one 2-D image comprises an establishment of a 2-D reference image, wherein the 2-D reference image is assigned to the at least one 3-D reference image.

8. The method of claim 1, wherein the visualizing of the at least one characteristic variable in the at least one 2-D image comprises:
   segmenting the at least one 2-D image according to the at least one vessel, and
   masking the at least one characteristic variable in the at least one 2-D image after the segmenting.

9. The method of claim 1, wherein the at least one characteristic variable is visualized color-coded in the at least one 2-D image.

10. The method of claim 1, wherein the visualizing of the at least one characteristic variable in the at least one 2-D image comprises a projection of the at least one characteristic variable onto the at least one 2-D image.

11. The method of claim 1, wherein the at least one characteristic variable of a control unit of the C-arm X-ray device is provided which, according to the at least one characteristic variable, is configured to establish control commands and wherein the control unit is configured to move the C-arm X-ray device in accordance with the control commands at least through an angle and wherein the C-arm X-ray device is configured to acquire a further 2-D image in accordance with the control commands.

12. The method of claim 1, wherein the image information system comprises an atlas, wherein the atlas comprises at least one depiction of the at least one 3-D reference image and wherein the determining includes applying the atlas to the at least one 2-D image to determine the at least one 3-D reference image.

13. The method of claim 1, wherein the image information system comprises an artificial neural network, wherein the determining of the at least one 3-D reference image includes training the artificial neural network through applying of the artificial neural network to the at least one 2-D image and wherein the determining includes applying the artificial neural network to the at least one 2-D image to determine the at least one 3-D reference image.

14. A non-transitory computer program product, directly loadable into a memory store of a programmable computer unit, including program code segments to carry out the method of claim 1 when the program code segments are executed in the computer unit.

15. The method of claim 1, wherein at least one metaparameter is assigned to the at least one 2-D image, wherein the at least one metaparameter is used in determining the at least one 3-D reference image and wherein the at least one metaparameter comprises at least one parameter of:
- an item of metainformation regarding the acquiring of the at least one 2-D image via the C-arm X-ray device,
- a vessel designation of the at least one vessel, and
- a cardiac phase of the patient.

16. The method of claim 3, wherein the at least one metaparameter comprises the vessel designation of the at least one vessel and the vessel designation comprising at least one parameter of:
- a vessel diameter of the at least one vessel,
- a maximum curvature of the at least one vessel, and
- a length of the at least one vessel.

17. The method of claim 1, wherein the determining of the at least one 3-D reference image by applying of the image information system to the at least one 2-D image comprises:
- segmenting the at least one 2-D image according to the at least one vessel, and
- applying the image information system to the at least one segmented 2-D image.

18. The method of claim 1, wherein the determining of the at least one 3-D reference image by applying of the image information system to the at least one 2-D image comprises an establishment of a 2-D reference image, wherein the 2-D reference image is assigned to the at least one 3-D reference image.

19. The method of claim 1, wherein the visualizing of the at least one characteristic variable in the at least one 2-D image comprises:
- segmenting the at least one 2-D image according to the at least one vessel, and
- masking the at least one characteristic variable in the at least one 2-D image after the segmenting.

20. The method of claim 1, wherein the at least one characteristic variable is visualized color-coded in the at least one 2-D image.

21. The method of claim 1, wherein the visualizing of the at least one characteristic variable in the at least one 2-D image comprises a projection of the at least one characteristic variable onto the at least one 2-D image.

22. The method of claim 1, wherein the image information system comprises an atlas, wherein the atlas comprises at least one depiction of the at least one 3-D reference image and wherein the determining includes applying the atlas to the at least one 2-D image to determine the at least one 3-D reference image.

23. The method of claim 1, wherein the image information system comprises an artificial neural network, wherein the determining of the at least one 3-D reference image includes training the artificial neural network through applying of the artificial neural network to the at least one 2-D image and wherein the determining includes applying the artificial neural network to the at least one 2-D image to determine the at least one 3-D reference image.

24. A non-transitory computer readable medium including program code for carrying out the method of claim 1 when the program code is run on a computer.

25. The method of claim 1, wherein the acquiring of the at least one 2-D image comprises subtracting a non-contrast-enhanced 2-D image from an angiographic 2-D image.

* * * * *